(12) United States Patent
Li et al.

(10) Patent No.: US 9,523,628 B2
(45) Date of Patent: Dec. 20, 2016

(54) METHOD AND APPARATUS FOR DETERMINING SEPARATION EFFICIENCY OF CYCLONE SEPARATOR

(71) Applicants: State Grid Corporation of China, Beijing (CN); North China Electric Power Research Institute Co. Ltd., Beijing (CN)

(72) Inventors: Jinjing Li, Beijing (CN); Zhanguo Li, Beijing (CN); Zhenning Zhao, Beijing (CN); Shuo Yang, Beijing (CN)

(73) Assignees: North China Electric Power Research Institute Co., Ltd., Beijing (CN); State Grid Corporation of China, Beijing (CN)

( * ) Notice: Subject to any disclaimer, the term of this patent is extended or adjusted under 35 U.S.C. 154(b) by 548 days.

(21) Appl. No.: 14/067,790

(22) Filed: Oct. 30, 2013

(65) Prior Publication Data

US 2014/0122021 A1 May 1, 2014

(30) Foreign Application Priority Data

Oct. 31, 2012 (CN) .......................... 2012 1 0427928

(51) Int. Cl.
  *G06F 17/18* (2006.01)
  *G01N 1/22* (2006.01)
  *G01N 15/02* (2006.01)

(52) U.S. Cl.
  CPC ......... *G01N 1/2211* (2013.01); *G01N 15/0255* (2013.01)

(58) Field of Classification Search
  CPC ........... B04C 3/04; B01J 38/72; C10G 11/182; C10G 2/32; C10G 2/342; C10G 31/08; C10G 31/09; C10G 32/02
  See application file for complete search history.

(56) References Cited

U.S. PATENT DOCUMENTS 4,342,640 A * 8/1982 Lewis .................... C10G 32/02
  208/177
5,035,910 A * 7/1991 Jones ...................... A23J 1/142
  426/417
(Continued)

FOREIGN PATENT DOCUMENTS

CN 101666717 A 3/2010
CN 102494881 A 6/2012
(Continued)

OTHER PUBLICATIONS

First Office Action and search report issued on Sep. 21, 2015 for Chinese patent application No. 201210427928.9, 10 pages.
(Continued)

*Primary Examiner* — Elias Desta
(74) *Attorney, Agent, or Firm* — Schwabe, Williamson & Wyatt, P.C.

(57) ABSTRACT

The present invention provides a method and an apparatus for determining separation efficiency of a cyclone separator. The method comprises: collecting solid particles separated by a cyclone separator; performing a particle size analysis for the collected solid particles; calculating feature parameters of the collected solid particles according to a result of the particle size analysis, wherein the feature parameters are values representing particle size and particle size uniformity of the solid particles; and determining a separation efficiency corresponding to the feature parameters of the collected solid particles as a separation efficiency of the cyclone separator, according to a predetermined correspondence between feature parameter and separation efficiency. The present invention avoids the difficulty in directly measuring the material concentrations at the inlet and the outlet of the cyclone separator and has a small interference with the apparatus. In addition, the test requires a simple operation and has a good repeatability.

12 Claims, 5 Drawing Sheets

(56) References Cited

U.S. PATENT DOCUMENTS 5,055,202 A * 10/1991 Carroll ............... B01D 17/0214
137/88
6,673,133 B2 * 1/2004 Sechrist .................... B04C 3/04
55/348

FOREIGN PATENT DOCUMENTS

| CN | 103335925 A | 10/2013 |
|---|---|---|
| JP | H0493610 A | 3/1992 |
| JP | H07218333 A | 8/1995 |
| JP | 3117865 B2 | 10/2000 |
| JP | 2008224551 A | 9/2008 |

OTHER PUBLICATIONS

Zhou L-S., et al., "Mathematical Model of Separation Efficiency on Cyclone Separator; Boiler Technology," Dec. 2011, 3 pages, vol. 42, No. 6, China.
Liden, Göran & Gudmundsson, Anders. "Semi-empirical modelling to generalise the dependence of cyclone collection efficiency on operating conditions and cyclone design." Journal of Aerosol Science. vol. 28, Issue 5, Jul. 1997, pp. 853-874.

* cited by examiner

METHOD AND APPARATUS FOR DETERMINING SEPARATION EFFICIENCY OF CYCLONE SEPARATOR

FIELD OF THE INVENTION

The present invention relates to separation technologies, and particularly, to a method and an apparatus for determining separation efficiency of a cyclone separator.

BACKGROUND OF THE INVENTION

The circulating fluidized bed boiler is a boiler which combusts coals and other low grade fuels using a principle of circulating fluidized bed reactor. As illustrated in FIG. 1, the circulating fluidized bed boiler is mainly composed of a furnace, a cyclone separator, a loop seal, a flue gas channel, a deduster, an induced draft fan, etc. The circulating fluidized bed boiler is widely used in the fields of industrial steam supply and thermal power generation, and it has prominent advantages in the aspects of environmental protection and pollutant comprehensive treatment.

The material balance system is apparatus and component for maintaining the gas-solid flow condition in the circulating fluidized bed boiler, and the cyclone separator is the critical component of the material balance system in the circulating fluidized bed boiler. The separation efficiency is an important index reflecting the separation performance of the cyclone separator, and the higher the separation efficiency, the better the separation performance. Therefore, the separation performance of the cyclone separator can be determined through a calculation of the separation efficiency. The separation efficiency may be acquired by directly calculating material concentrations (mass of solid particles contained in the gas of unit volume) at an inlet and an outlet of the cyclone separator. For example, a patent solution with an application number CN200910024109.8 proposes the following measurement method: obtaining a material concentration $\rho_{in}$ at the inlet of the cyclone separator by measuring a pressure difference between a middle portion and an upper portion of the boiler furnace, and obtaining a material concentration $\rho_{out}$ at the outlet of the cyclone separator by measuring a flue flow rate at the outlet of the cyclone separator, then calculating the separation efficiency of the cyclone separator as $cyc=(1-\rho_{out}/\rho_{in})\times 100\%$, and finally analyzing the separation performance of the cyclone separator according to the separation efficiency. The method analyzes the separation performance by directly calculating the separation efficiency. But in commercial units, it is difficult to accurately calculate the material concentration at the inlet of the cyclone separator according to the pressure difference between the middle portion and the upper portion of the boiler furnace, and it is also hard to measure the flue flow rate and the material concentration at the outlet of the cyclone separator under the condition of the prior art, and the measurement process will interfere with the gas flow and combustion in the boiler, thus the method is not so practically operable.

It is important to determine the separation efficiency of the cyclone separator, so as to guide the boiler operation, and ensure stable flow and combustion state in the circulating fluidized bed boiler. However, at present, measures for effectively measuring the separation efficiency of the cyclone separator are absent.

SUMMARY OF THE INVENTION

A main object of the embodiments of the present invention is to provide a method and an apparatus for determining separation efficiency of a cyclone separator, so as to overcome the deficiency of the prior art that the separation efficiency of the cyclone separator cannot be measured effectively.

In order to achieve the above object, the embodiments of the present invention provide a method for determining separation efficiency of a cyclone separator, comprising:

collecting solid particles separated by the cyclone separator;

performing a particle size analysis for the collected solid particles;

calculating feature parameters of the collected solid particles according to a result of the particle size analysis, wherein the feature parameters are values representing particle size and particle size uniformity of the solid particles; and determining a separation efficiency corresponding to the feature parameters of the collected solid particles as a separation efficiency of the cyclone separator, according to a predetermined correspondence between feature parameter and separation efficiency.

Preferably, in the method, the step of collecting the solid particles separated by the cyclone separator comprises:

collecting solid particles captured by the cyclone separator during the separation; or collecting solid particles escaping from the cyclone separator during the separation.

Preferably, in the method, the step of performing the particle size analysis for the collected solid particles comprises:

performing a particle size measurement for the collected solid particles, and counting proportions of particles of different particle sizes in the collected solid particles; or performing a particle size measurement for the collected solid particles, and counting accumulated proportions of particles of different particle sizes in the collected solid particles.

Preferably, in the method, the step of calculating the feature parameters of the collected solid particles according to the result of the particle size analysis comprises:

determining the feature parameters of the collected solid particles by fitting a function according to the result of the particle size analysis.

Preferably, in the method, the feature parameters are particle size average value and particle size standard deviation, and the function is a log-normal distribution function:

$$f(d_p) = \frac{1}{\sqrt{2\pi}\, lg\sigma_g} \exp\left(-\frac{(lgd_p - lgd_{50})^2}{2lg^2\sigma_g}\right)$$

wherein, $d_p$ any particle size in the result of the particle size analysis, $f(d_p)$ is a proportion of particles of particle size $d_p$ in the result of the particle size analysis, $d_{50}$ is a particle size average value of the collected solid particles, and $\sigma_g$ is a particle size standard deviation of the collected solid particles.

Preferably, in the method, the step of determining the separation efficiency corresponding to the feature parameters of the collected solid particles according to the predetermined correspondence between feature parameter and separation efficiency comprises:

determining the separation efficiency corresponding to the particle size average value and the particle size standard deviation of the collected solid particles according to a predetermined correspondence between the separation efficiency and the particle size average value, the particle size standard deviation.

Preferably, in the method, the feature parameters are particle size characteristic value and particle size uniformity coefficient, and the function is a Rosin-Rammler distribution function:

$$D(d_p)=100-100\exp[-(D_p/d_e)^n]$$

wherein, $d_p$ is any particle size in the result of the particle size analysis, $D(d_p)$ is an accumulated proportion of particles having particle sizes equal to or smaller than $d_p$ in the result of the particle size analysis, $d_e$ is a particle size characteristic value of the solid particles, and n is a particle size uniformity coefficient of the solid particles.

Preferably, in the method, the step of determining the separation efficiency corresponding to the feature parameters of the collected solid particles according to the predetermined correspondence between feature parameter and separation efficiency comprises:

determining the separation efficiency corresponding to the particle size characteristic value and the particle size uniformity coefficient of the collected solid particles according to a predetermined correspondence between the separation efficiency and the particle size characteristic value, the particle size uniformity coefficient.

Preferably, in the method, the cyclone separator is applied in a circulating fluidized bed boiler, and the solid particles are circulating ash particles captured by the cyclone separator, and/or flying ash particles escaping from the cyclone separator.

An apparatus for determining separation efficiency of a cyclone separator, comprising: a particle size analysis device, a parameter determination device and a separation efficiency determination device, wherein the particle size analysis device is configured to perform a particle size analysis for solid particles separated by a cyclone separator, and transmit a result of the particle size analysis to the parameter determination device;

the parameter determination device is configured to calculate feature parameters of the solid particles according to the result of the particle size analysis, and transmit the calculated feature parameters to the separation efficiency determination device, wherein the feature parameters are values representing particle size and particle size uniformity of the solid particles; and the separation efficiency determination device is configured to determine a separation efficiency corresponding to the feature parameters of the solid particles as a separation efficiency of the cyclone separator, according to a predetermined correspondence between feature parameter and separation efficiency.

Preferably, the particle size analysis device comprises a standard sieve, a sieve shaker and a sieving result analyzer, wherein the sieve shaker is configured to vibrate the standard sieve;

the standard sieve is configured to sieve particles of different particle sizes in the solid particles through vibration; and the sieving result analyzer is configured to count proportions and/or accumulated proportions of particles of different particle sizes in the solid particles according to a result of the sieving by the standard sieve, and transmit a result of the counting to the parameter determination device.

Preferably, the particle size analysis device comprises a laser diffraction particle size analyzer and a result output port, wherein the laser diffraction particle size analyzer is configured to count proportions and/or accumulated proportions of particles of different particle sizes in the solid particles; and the result output port is configured to transmit a result of the counting by the laser diffraction particle size analyzer to the parameter determination device.

Through the above technical solutions, by performing a particle size analysis for the solid particles separated by the cyclone separator, the present invention acquires the feature parameters capable of representing particle size and particle size uniformity of the solid particles separated by the cyclone separator, and determines the separation efficiency of the cyclone separator according to the predetermined correspondence between feature parameter and separation efficiency. The present invention does not calculate the separation efficiency by directly measuring the material concentrations at the inlet and the outlet of the cyclone separator, instead, it performs a particle size analysis for the solid particles separated by the cyclone separator to obtain the feature parameters, and then compares them with a predetermined standard correspondence to determine the separation efficiency of the cyclone separator. As compared with the prior art, the present invention avoids the difficulty in directly measuring the material concentrations at the inlet and the outlet of the cyclone separator and has a very small interference with the apparatus. In addition, the test requires a simple operation and has a good repeatability.

BRIEF DESCRIPTION OF THE DRAWINGS

In order to more clearly describe the technical solutions in the prior art or the embodiments of the present invention, the drawings to be used in the descriptions of the prior art or the embodiments will be briefly introduced as follows. Obviously, the following drawings just illustrate some embodiments of the present invention, and a person skilled in the art can obtain other drawings from them without paying any creative effort.

DETAILED DESCRIPTION OF THE EMBODIMENTS

The technical solutions of the embodiments of the present invention will be clearly and completely described as follows with reference to the drawings. Obviously, those described herein are just parts of the embodiments of the present invention rather than all the embodiments. Based on the embodiments of the present invention, any other embodiment obtained by a person skilled in the art without paying any creative effort shall fall within the protection scope of the present invention.

Since measures for effectively measuring separation efficiency of a cyclone separator are absent in the prior art, the embodiments of the present invention provide a method and an apparatus for determining separation efficiency of a cyclone separator, so as to implement a method simply operable and capable of effectively determining the separation efficiency of the cyclone separator. The present invention will be described in details as follows with reference to the drawings.

A First Embodiment

Figure 2:
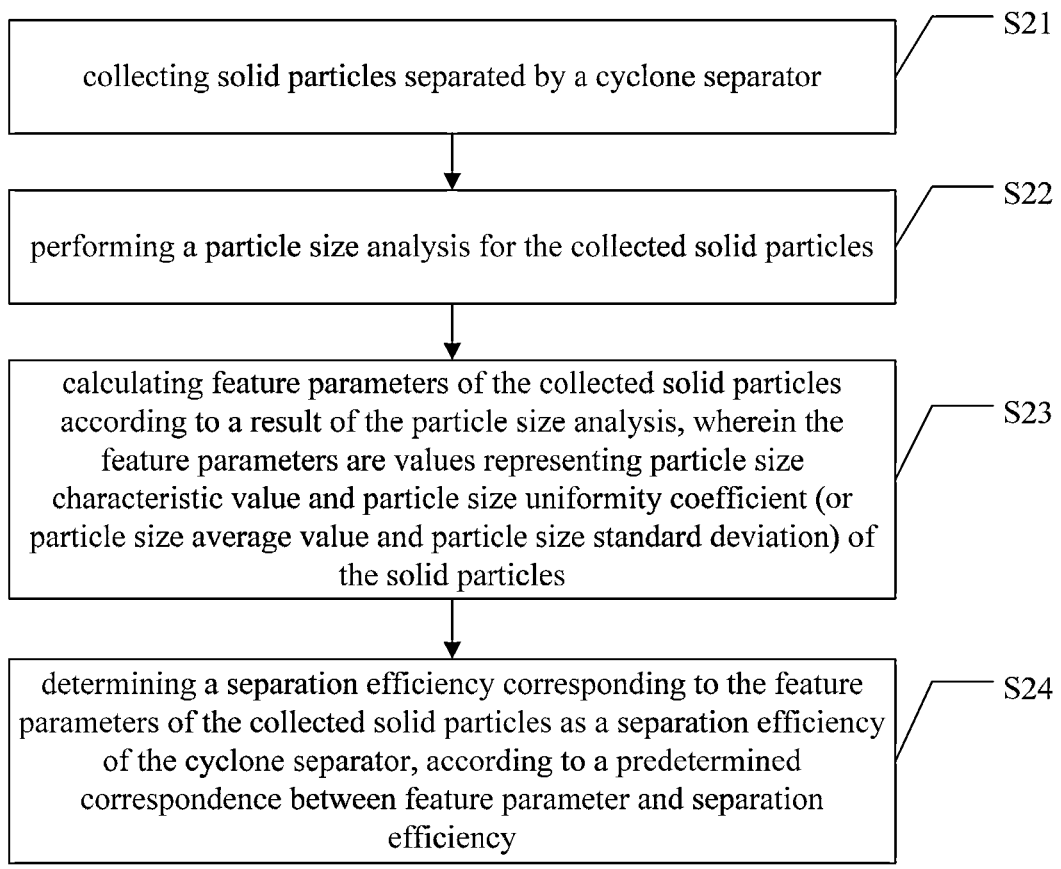
FIG. 2 shows a schematic diagram of a method for determining separation efficiency of a cyclone separator according to a first embodiment of the present invention.

This embodiment provides a method for determining separation efficiency of a cyclone separator. As illustrated in FIG. 2, the method comprises:

Step S21: collecting solid particles separated by a cyclone separator;

Step S22: performing a particle size analysis for the collected solid particles;

Step S23: calculating feature parameters of the collected solid particles according to a result of the particle size analysis, wherein the feature parameters are values representing particle size and particle size uniformity of the solid particles;

Step S24: determining a separation efficiency corresponding to the feature parameters of the collected solid particles as a separation efficiency of the cyclone separator, according to a predetermined correspondence between feature parameter and separation efficiency.

To be noted, the predetermined correspondence between feature parameter and separation efficiency is a one-to-one correspondence between feature parameter and separation efficiency obtained by measuring the feature parameters of the solid particles separated by a cyclone separator having known separation efficiency under a predetermined working condition. In the embodiment of the present invention, such correspondence is taken as a reference standard, and the feature parameters actually calculated according to the result of the particle size analysis are compared with the reference standard to determine an interval in which the separation efficiency corresponding to the calculated feature parameters falls, thereby determining the separation efficiency of the cyclone separator being tested. For example, the correspondence may be provided by the manufacturer of the cyclone separator: under a predetermined working condition, a plurality of groups of cyclone separators having different known separation efficiencies are tested to obtain the feature parameters of the separated solid particles, then a separation efficiency-feature parameter correspondence table is established and provided to the user as a reference standard for the cyclone separators of the same type.

To be noted, in order that the test result is comparable, when the cyclone separator is actually tested and the correspondence between feature parameter and separation efficiency is predetermined, the cyclone separator shall be under the same working condition. Only in this way, can the separation efficiency determined according to the predetermined correspondence and the actually calculated feature parameters really reflect the separation performance of the detected cyclone separator. For example, when the separation efficiency of the cyclone separator in the circulating fluidized bed boiler is to be determined, the manufacturer may provide a separation efficiency-feature parameter correspondence table acquired when the circulating fluidized bed boiler is under a certain predetermined working condition; and correspondingly, when the user wants to test the separation efficiency of the cyclone separator using the correspondence table, the test shall also be made when the circulating fluidized bed boiler is under the same working condition.

By performing a particle size analysis for the solid particles separated by the cyclone separator, the embodiment acquires the feature parameters capable of representing particle size and particle size uniformity of the solid particles separated by the cyclone separator, and determines the separation efficiency of the cyclone separator according to the predetermined correspondence between feature parameter and separation efficiency. The present invention does not calculate the separation efficiency by directly measuring the material concentrations at the inlet and the outlet of the cyclone separator, instead, it performs a particle size analysis for the solid particles separated by the cyclone separator to obtain the feature parameters, and then compares the feature parameters with the established standard correspondence to determine the separation efficiency of the cyclone separator. As compared with the prior art, the present invention avoids the difficulty in directly measuring the material concentrations at the inlet and the outlet of the cyclone separator and has a small interference with the apparatus. In addition, the test requires a simple operation and has a good repeatability.

Preferably, in step S21, collecting the solid particles separated by the cyclone separator comprises:

collecting solid particles captured by the cyclone separator during the separation; or collecting solid particles escaping from the cyclone separator during the separation.

Specifically, the separation performance of the cyclone separator is mainly reflected by a capacity of capturing fine particles. Under the same working condition, the higher the separation efficiency of the cyclone separator, the finer and more uniform the captured particles. For example, circulating ashes are ash particles captured by the cyclone separator and returned to the furnace by the loop seal, and when the circulating fluidized bed boiler is under the same working condition, the higher the separation efficiency of the cyclone separator, the finer and more uniform the captured circulating ash particles.

Similarly, the separation performance of the cyclone separator can also be obtained by analyzing the solid particles escaping from the cyclone separator during the separation. Under the same working condition, the higher the separation efficiency, the finer the solid particles escaping from the cyclone separator. For example, in the circulating fluidized bed boiler, flying ashes are ash particles escaping from the outlet of the cyclone separator to the flue gas channel, and generally, the flying ashes are finer and lighter than the circulating ashes. When the circulating fluidized bed boiler is under the same working condition, the higher the separation efficiency of the cyclone separator, the finer the escaped flying ashes.

Thus, the separation efficiency of the cyclone separator can be determined by analyzing the solid particles captured by the cyclone separator during the separation, or the solid particles escaping from the cyclone separator during the separation.

Preferably, in step S22, performing the particle size analysis for the collected solid particles comprises: performing a particle size measurement for the collected solid particles, and counting proportions of particles of different particle sizes in the collected solid particles.

Preferably, in step S22, performing the particle size analysis for the collected solid particles comprises: performing a particle size measurement for the collected solid particles, and counting accumulated proportions of particles of different particle sizes in the collected solid particles.

Specifically, the accumulated proportions of particles of different particle sizes in the collected solid particles mean accumulating to sum up, for each particle size of the collected solid particles, proportions of all particles having particle sizes equal to or smaller than the particle size.

Figure 3:
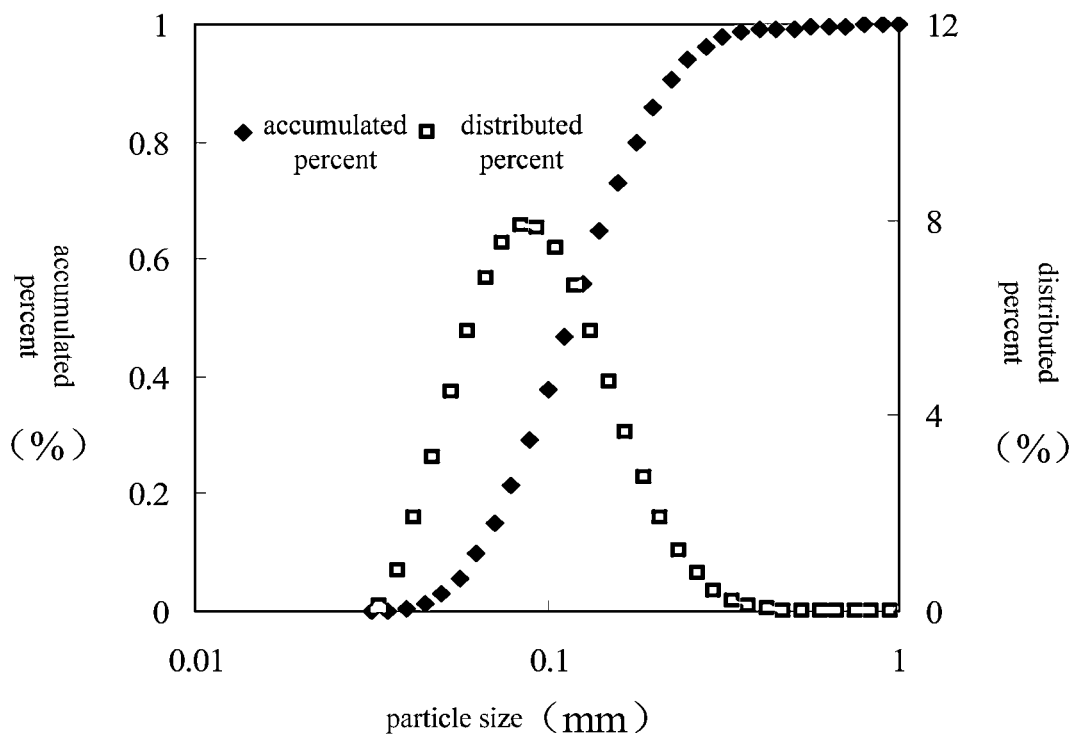
FIG. 3 shows a graph obtained according to a result of a particle size analysis for circulating ash particles according to the first embodiment of the present invention.

For example, FIG. 3 shows a graph obtained according to a result of a particle size analysis for an amount of circulating ash particles captured by a cyclone separator in a circulating fluidized bed boiler and collected as samples, wherein distributed percent means proportion of circulating ash particles of different particle sizes in the circulating ash samples, and accumulated percent means accumulated proportion of circulating ash particles having particle sizes equal to or smaller than each particle size interval in the circulating ash samples.

Preferably, in step S23, calculating the feature parameters of the collected solid particles according to the result of the particle size analysis comprises:

determining the feature parameters of the collected solid particles by fitting a function according to the result of the particle size analysis.

Specifically, proportions or accumulated proportions of particles of different particle sizes in the collected solid particles can be obtained based on the particle size analysis in step S22, and then the feature parameters of the collected solid particles can be determined by fitting a function according to the result of the particle size analysis.

Preferably, the feature parameters are particle size average value and particle size standard deviation, and the function is a log-normal distribution function:

$$f(d_p) = \frac{1}{\sqrt{2\pi}\, lg\sigma_g} \exp\left(-\frac{(lgd_p - lgd_{50})^2}{2lg^2\sigma_g}\right)$$

wherein, $d_p$ is any particle size in the result of the particle size analysis, $f(d_p)$ is a proportion of particles of particle size $d_p$ in the result of the particle size analysis, $d_{50}$ is a particle size average value of the collected solid particles, and $\sigma_g$ is a particle size standard deviation of the collected solid particles.

Specifically, $d_p$ and $f(d_p)$ in one-to-one correspondence are determined according to the result of the particle size analysis for the proportions of particles of different particle sizes in the collected solid particles, and a fitting is performed using the log-normal distribution function, thereby the feature parameters, i.e., the particle size average value $d_{50}$ and the particle size standard deviation $\sigma_g$ are finally determined, wherein the particle size average value $d_{50}$ represents an average particle size of all of the collected solid particles, and the particle size standard deviation $\sigma_g$ represents a particle size uniformity of all of the collected solid particles; and the smaller the particle size average value $d_{50}$, the smaller the particle size standard deviation $\sigma_g$, which means that the better the separation performance of the cyclone separator, the higher the separation efficiency.

Preferably, in step S24, determining the separation efficiency corresponding to the feature parameters of the collected solid particles according to the predetermined correspondence between feature parameter and separation efficiency comprises:

determining the separation efficiency corresponding to the particle size average value and the particle size standard deviation of the collected solid particles according to a predetermined correspondence between the separation efficiency and the particle size average value, the particle size standard deviation.

Specifically, when the selected feature parameters are the particle size average value and the particle size standard deviation, the selected reference standard shall also be consistent therewith, i.e., the reference standard shall be the predetermined correspondence between the separation efficiency and the particle size average value, the particle size standard deviation.

Preferably, the feature parameters are the particle size characteristic value and a particle size uniformity coefficient, and the function is a Rosin-Rammler distribution function:

$$D(d_p) = 100 - 100\exp[-(D_p/d_e)^n]$$

wherein, $d_p$ is any particle size in the result of the particle size analysis, $D(d_p)$ is an accumulated proportion of particles having particle sizes equal to or smaller than $d_p$ in the result of the particle size analysis, $d_e$ is a particle size characteristic value of the solid particles, and n is a particle size uniformity coefficient of the solid particles.

Specifically, $d_p$ and $D(d_p)$ in one-to-one correspondence are determined according to the accumulated proportions of particles of different particle sizes in the collected solid particles, and a fitting is performed using the Rosin-Rammler distribution function, thereby the feature parameters, i.e., the particle size characteristic value $d_e$ and the particle size uniformity coefficient n are determined, wherein the particle size characteristic value $d_e$ represents an characteristic particle size of all of the collected solid particles, and the particle size uniformity coefficient n represents a particle size uniformity of all of the collected solid particles; and the smaller the particle size characteristic value $d_e$, the larger the particle size uniformity coefficient n, which means that the better the separation performance of the cyclone separator, the higher the separation efficiency.

Preferably, in step S24, determining the separation efficiency corresponding to the feature parameters of the collected solid particles according to the predetermined correspondence between feature parameter and separation efficiency comprises:

determining the separation efficiency corresponding to the particle size characteristic value and the particle size uniformity coefficient of the collected solid particles according to a predetermined correspondence between the separation efficiency and the particle size characteristic value, the particle size uniformity coefficient.

Specifically, when the selected feature parameters are the particle size uniformity coefficient value and the particle size uniformity coefficient, the selected reference standard shall also be consistent therewith, i.e., the reference standard shall be the predetermined correspondence between the separation efficiency and the particle size characteristic value, the particle size uniformity coefficient.

Preferably, the cyclone separator is applied in the circulating fluidized bed boiler, and the solid particles are circulating ash particles captured by the cyclone separator, and/or flying ash particles escaping from the cyclone separator.

Figure 1:
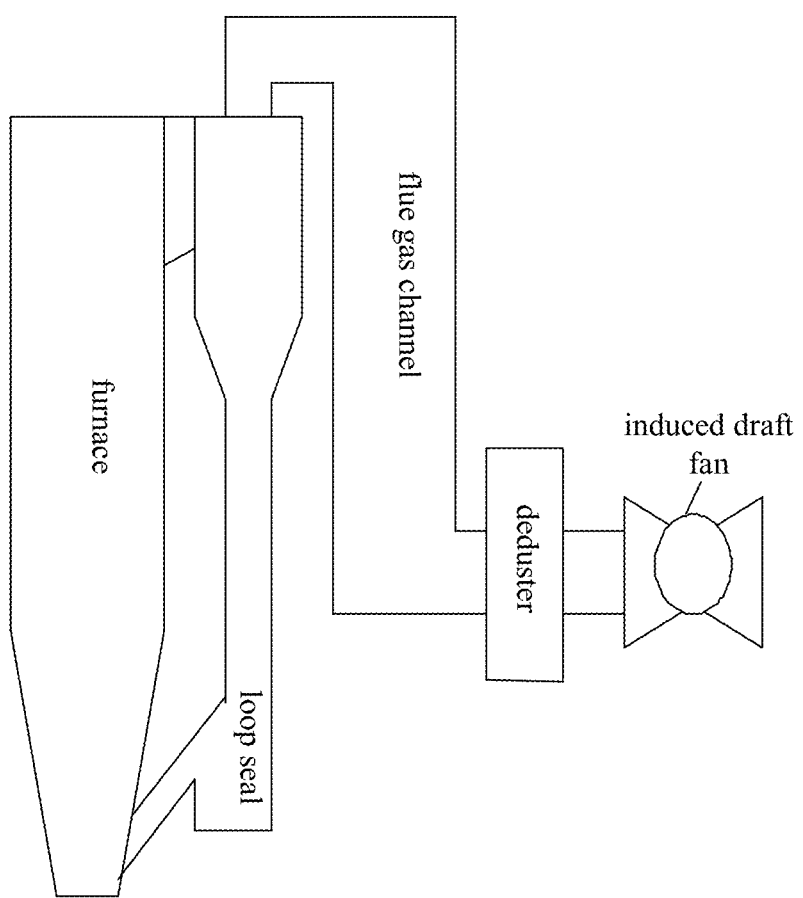
FIG. 1 shows a schematic diagram of a structure of a circulating fluidized bed boiler according to the related art.

Specifically, when the separation efficiency of the cyclone separator applied in the circulating fluidized bed boiler is to be tested, an amount of circulating ash particles may be collected as samples at the loop seal as illustrated in FIG. 1, and after a particle size analysis for the samples, the feature parameters of the samples are calculated according to a result of the particle size analysis, then a separation efficiency corresponding to the feature parameters of the samples is determined as the separation efficiency of the detected cyclone separator according to a predetermined correspondence between feature parameter and separation efficiency of the circulating ash particles. Similarly, the flying ash particles may also be used for a test, and the test process is similar to that of the circulating ash particles, which is omitted herein.

A Second Embodiment

Figure 4:
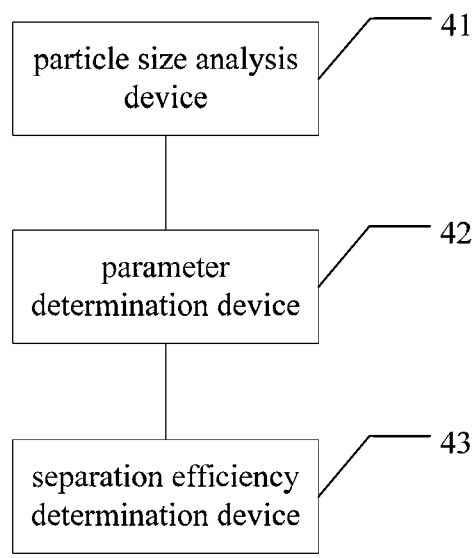
FIG. 4 shows an apparatus for determining separation efficiency of a cyclone separator according to a second embodiment of the present invention.

The embodiment provides an apparatus for determining separation efficiency of a cyclone separator. As illustrated in FIG. 4, the apparatus comprises a particle size analysis device 41, a parameter determination device 42 and an separation efficiency determination device 43, wherein the particle size analysis device 41 is configured to perform a particle size analysis for solid particles separated by a cyclone separator, and transmit a result of the particle size analysis to the parameter determination device 42;

the parameter determination device 42 is configured to calculate feature parameters of the solid particles according to the result of the particle size analysis, and transmit the calculated feature parameters to the separation efficiency determination device 43, wherein the feature parameters are values representing particle size and particle size uniformity of the solid particles; and the separation efficiency determination device 43 is configured to determine a separation efficiency corresponding to the feature parameters of the collected solid particles as a separation efficiency of the cyclone separator, according to a predetermined correspondence between feature parameter and separation efficiency.

Specifically, the particle size analysis device 41 is capable of measuring the particle sizes of the solid particles and counting the result of the particle size measurement. It may be a particle size test device based on a particle size test principle such as sieving and weighing, laser particle diameter analysis, or coherent spectrum particle size test.

The parameter determination device 42 is a software program or a computer device capable of calculating the feature parameters of the solid particles according to the result of the particle size analysis. For example, it may be a software program capable of obtaining a particle size average (or characteristic) value, a particle size standard deviation or a particle size uniformity coefficient of the solid particles according to the result of the particle size analysis by fitting a function; and the separation efficiency determination device 43 is a software program or a computer device storing a predetermined correspondence between feature parameter and separation efficiency, and capable of determining, according to the correspondence, a separation efficiency corresponding to the feature parameters calculated by the parameter determination device 42 as a separation efficiency of the cyclone separator to be detected.

Preferably, the particle size analysis device 41 specifically comprises a standard sieve, a sieve shaker, and a sieving result analyzer, wherein the sieve shaker is configured to vibrate the standard sieve;

the standard sieve is configured to sieve particles of different particle sizes in the solid particles through vibration; and the sieving result analyzer is configured to count proportions and/or accumulated proportions of particles of different particle sizes in the solid particles according to a result of the sieving by the standard sieve, and transmit a result of the counting to the parameter determination device.

Figure 5:
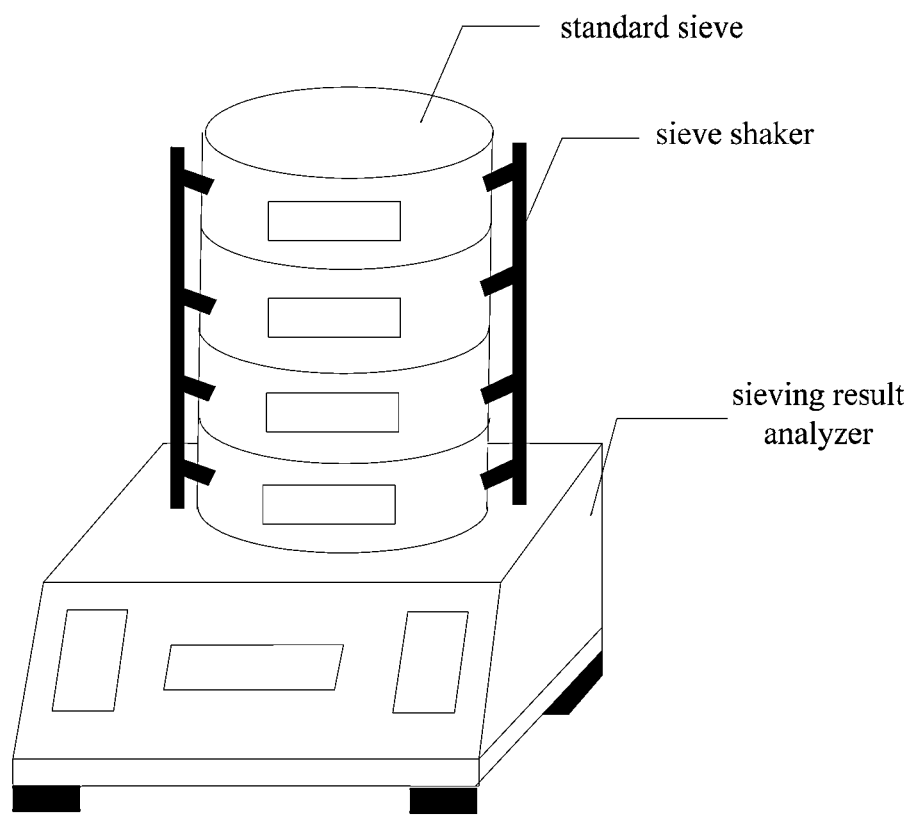
FIG. 5 shows a schematic diagram of a particle size analysis device based on a principle of sieving and weighing according to the second embodiment of the present invention.

Specifically, the particle size analysis device is based on a principle of sieving and weighing. As illustrated in FIG. 5, the particle size analysis device comprises a standard sieve, a sieve shaker and a sieving result analyzer, wherein standard sieves having different mesh sizes may be selected for different solid particles to be tested. For example, when circulating ash particles in the circulating fluidized bed boiler are to be tested, a group of sieves having mesh sizes 0.500 mm, 0.250 mm, 0.180 mm, 0.125 mm, 0.090 mm, 0.0750 mm, 0.0450 mm and 0.0308 mm may be used; and when flying ash particles in the circulating fluidized bed boiler are to be tested, a group of sieves having mesh sizes 0.100 mm, 0.074 mm, 0.061 mm, 0.050 mm, 0.045 mm, 0.040 mm and 0.0308 mm may be used.

Preferably, the particle size analysis device 41 comprises a laser diffraction particle size analyzer and a result output port; wherein the laser diffraction particle size analyzer is configured to count proportions and/or accumulated proportions of particles of different particle sizes in the solid particles; and the result output port is configured to transmit a result of the counting by the laser diffraction particle size analyzer to the parameter determination device.

Figure 6:
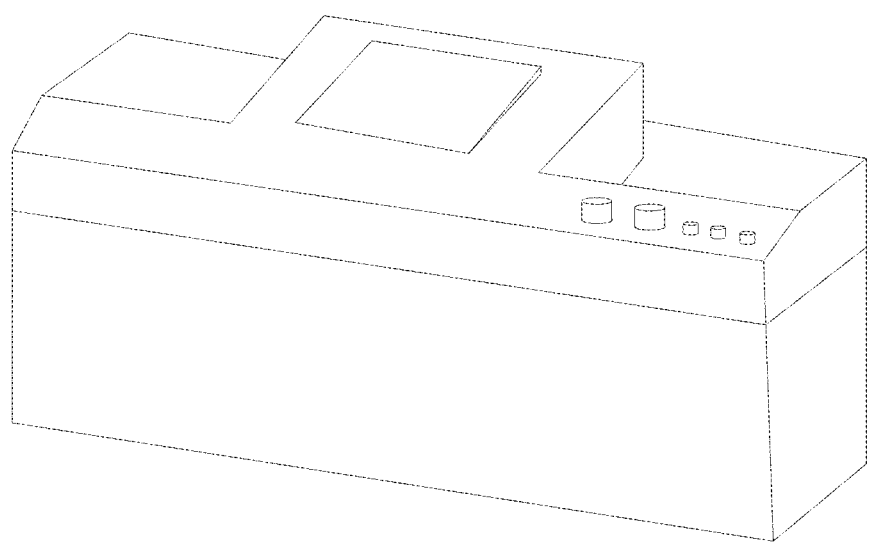
FIG. 6 shows a schematic diagram of a particle size analysis device based on a principle of laser diffraction particle size test according to the second embodiment of the present invention.

Specifically, the particle size analysis device is based on a principle of laser diffraction particle size test, and FIG. 6 illustrates a laser diffraction particle size analyzer.

In conclusion, the method and apparatus for determining the separation efficiency of the cyclone separator provided by the embodiments of the present invention have the following beneficial effects:

1) the present invention does not calculate the separation efficiency by directly measuring the material concentrations at the inlet and the outlet of the cyclone separator, instead, it performs a particle size analysis for the solid particles separated by the cyclone separator to obtain the feature parameters, and then compares the feature parameters with the predetermined standard correspondence to determine the separation efficiency of the cyclone separator, thereby avoiding the difficulty in directly measuring the material concentrations at the inlet and the outlet of the cyclone separator; and 2) the present invention has a small interference with the apparatus in the process of determining the separation efficiency of the cyclone separator, and the operation is simple with a good repeatability.

The above specific embodiments make further detailed description of the object, the technical solution and the beneficial effects of the present invention. It shall be appreciated that they are just specific embodiments of the present invention, rather than limitations to the protection scope of the present invention. Any amendment, equivalent replacement, modification, etc. made within the spirit and principle of the present invention shall fall within the protection scope of the present invention.

What is claimed is:

1. A method for determining a separation efficiency of a cyclone separator, comprising:
   with respect to a collected solid particles separated by the cyclone separator;
   performing, by a processor in a particle size analysis device, a particle size analysis for the collected solid particles;
   calculating, by a processor in a parameter determination device, a feature parameters of the collected solid particles according to a result of the particle size analysis, wherein the feature parameters are values representing particle size and particle size uniformity of the collected solid particles; and
   determining, by a processor in a separation efficiency determination device, a separation efficiency corresponding to the feature parameters of the collected solid particles as the separation efficiency of the cyclone separator, according to a predetermined correspondence between the feature parameters and the separation efficiency.

2. The method according to claim 1, wherein the collected solid particles are collected
   during a separation by the cyclone separator or are collected
   after escaping from the cyclone separator during the separation.

3. The method according to claim 1, wherein performing the particle size analysis, by the processor in the particle size analysis device, for the collected solid particles comprises:
   performing, by the processor in the particle size analysis device, a particle size measurement for the collected solid particles, and counting, by the processor in the particle size analysis device, a proportions of particles of different particle sizes in the collected solid particles; or
   performing, by the processor in the particle size analysis device, a particle size measurement for the collected solid particles, and counting, by the processor in the particle size analysis device, an accumulated proportions of particles of different particle sizes in the collected solid particles.

4. The method according to claim 3, wherein calculating, by the processor in the parameter determination device, the feature parameters of the collected solid particles according to the result of the particle size analysis comprises:
   determining, by the processor in the parameter determination device, the feature parameters of the collected solid particles by fitting a function according to the result of the particle size analysis.

5. The method according to claim 4, wherein the feature parameters are a particle size average value of the collected solid particles and a particle size standard deviation, and the function is a log-normal distribution function:

$$f(d_p) = \frac{1}{\sqrt{2\pi}\, lg\sigma_g} \exp\left(-\frac{(lgd_p - lgd_{50})^2}{2lg^2\sigma_g}\right)$$

wherein, $d_p$ is any particle size in the result of the particle size analysis, $f(d_p)$ is a proportion of particles of particle size $d_p$ in the result of the particle size analysis, $d_{50}$ is the particle size average value of the collected solid particles, and $\sigma_g$ is a particle size standard deviation of the collected solid particles.

6. The method according to claim 5, wherein determining, by the processor in the separation efficiency determination device, the separation efficiency corresponding to the feature parameters of the collected solid particles according to the predetermined correspondence between the feature parameters and the separation efficiency comprises:
   determining, by the processor in the separation efficiency determination device, the separation efficiency corresponding to the particle size average value and the particle size standard deviation of the collected solid particles according to a predetermined correspondence between the separation efficiency and the particle size average value, and the particle size standard deviation.

7. The method according to claim 4, wherein the feature parameters are a particle size characteristic value of the solid particles and a particle size uniformity coefficient, and the function is a Rosin-Rammler distribution function:

$$D(d_p) = 100 - 100\exp[-(D_p/d_e)^n]$$

wherein, $d_p$ is any particle size in the result of the particle size analysis, $D(d_p)$ is an accumulated proportion of particles having particle sizes equal to or smaller than $d_p$ in the result of the particle size analysis, $d_e$ is the particle size characteristic value of the collected solid particles, and n is a particle size uniformity coefficient of the collected solid particles.

8. The method according to claim 7, wherein the step of determining, by the processor in the separation efficiency determination device, the separation efficiency corresponding to the feature parameters of the collected solid particles according to the predetermined correspondence between the feature parameters and the separation efficiency comprises:
   determining, by the processor in the separation efficiency determination device, the separation efficiency corresponding to the particle size characteristic value and the particle size uniformity coefficient of the collected solid particles according to a predetermined correspondence between the separation efficiency and the particle size characteristic value of the collected solid particles, and the particle size uniformity coefficient.

9. The method of claim 1, wherein the cyclone separator is applied in a circulating fluidized bed boiler, and the solid particles comprise circulating ash particles captured by the cyclone separator, and/or flying ash particles escaping from the cyclone separator.

10. An apparatus for determining a separation efficiency of a cyclone separator, comprising: a particle size analysis device, a parameter determination device and a separation efficiency determination device, wherein
    the particle size analysis device is configured to perform a particle size analysis for a solid particles separated by the cyclone separator, and transmit a result of the particle size analysis to the parameter determination device;
    the parameter determination device is configured to calculate a feature parameters of the solid particles according to the result of the particle size analysis, and transmit the feature parameters to the separation efficiency determination device, wherein the feature parameters are values representing a particle size and a particle size uniformity of the solid particles; and
    the separation efficiency determination device is configured to determine the separation efficiency corresponding to the feature parameters of the solid particles as the separation efficiency of the cyclone separator, according to a predetermined correspondence between the feature parameters and the separation efficiency.

11. The apparatus according to claim 10, wherein the particle size analysis device comprises a standard sieve, a sieve shaker and a sieving result analyzer, wherein
- the sieve shaker is configured to vibrate the standard sieve;
- the standard sieve is configured to sieve particles of different particle sizes in the solid particles through vibration; and
- the sieving result analyzer is configured to count a proportions and/or an accumulated proportions of particles of different particle sizes in the solid particles according to a result of the sieving by the standard sieve as a sieving result, and transmit the sieving result to the parameter determination device.

12. The apparatus according to claim 10, wherein the particle size analysis device comprises a laser diffraction particle size analyzer and a result output port, wherein
- the laser diffraction particle size analyzer is configured to count a proportions and/or an accumulated proportions of particles of different particle sizes in the solid particles as a laser counting result; and
- the result output port is configured to transmit the laser counting result to the parameter determination device.

* * * * *